United States Patent [19]
Girvin et al.

[11] Patent Number: 5,903,347
[45] Date of Patent: *May 11, 1999

[54] PARTICLE COUNTER EMPLOYING A CHROMIUM BASED SOLID-STATE LASER WITH AN INTRACAVITY VIEW VOLUME

[75] Inventors: Kenneth L. Girvin; Richard K. DeFreez, both of Grants Pass, Oreg.

[73] Assignee: Met One, Inc., Grants Pass, Oreg.

[ * ] Notice: This patent is subject to a terminal disclaimer.

[21] Appl. No.: 08/876,136

[22] Filed: Jun. 23, 1997

Related U.S. Application Data

[63] Continuation-in-part of application No. 08/614,814, Mar. 8, 1996, Pat. No. 5,642,193.

[51] Int. Cl.$^6$ .................................................. G01N 15/06
[52] U.S. Cl. ................................................................ 356/339
[58] Field of Search ............................... 356/336, 338, 356/339

[56] References Cited

U.S. PATENT DOCUMENTS

| | | | |
|---|---|---|---|
| 4,571,079 | 2/1986 | Knollenberg | 356/336 |
| 4,594,715 | 6/1986 | Knollenberg | 372/22 |
| 4,685,802 | 8/1987 | Saito et al. | 356/339 |
| 4,746,215 | 5/1988 | Gross | 356/339 |
| 4,798,465 | 1/1989 | Knollenberg | 356/336 |
| 5,033,851 | 7/1991 | Sommer | 356/338 |
| 5,084,879 | 1/1992 | Suzuki et al. | 372/22 |
| 5,085,500 | 2/1992 | Blesener | 356/338 |
| 5,092,675 | 3/1992 | Sommer | 356/338 |
| 5,121,988 | 6/1992 | Blesener et al. | 356/442 |
| 5,135,304 | 8/1992 | Miles et al. | 356/301 |
| 5,191,588 | 3/1993 | Dacquay | 372/22 |
| 5,317,447 | 5/1994 | Baird et al. | 359/328 |
| 5,483,546 | 1/1996 | Johnson et al. | 372/10 |
| 5,642,193 | 6/1997 | Girvin et al. | |
| 5,726,753 | 3/1998 | Sandberg | 356/338 |

OTHER PUBLICATIONS

Burton G. Schuster et al., "Detection and Sizing of Small Particles in an Open Cavity Gas Laser", *Applied Optics*, vol. 11, No. 7, pp. 1515–1520 (Jul. 1972).

Robert G. Knollenberg et al., "Open Cavity Laser 'Active' Scattering Particle Spectrometry from 0.05 to 5 Microns", *Fine Particles—Aerosol Generation, Measurement, Sampling, and Analysis*, Academic Press, pp. 669–696 (May 1975).

*Primary Examiner*—Richard A. Rosenberger
*Attorney, Agent, or Firm*—Thomas Schneck

[57] ABSTRACT

A particle detector employs a resonant cavity having a chromium doped colquiriite crystal lasing medium, such as an Cr:LiSrAlF$_6$ crystal, adjacent to an intra-cavity view volume. The resonant cavity is defined by two spaced apart mirrors, with the crystal positioned between them, defining a light path through the crystal, but most of the light does not escape past the mirrors. The view volume is positioned in the light path, between the first mirror and the laser medium, to introduce particles into the resonant cavity so that light impinging thereupon produces scattered light. A detector is disposed to sense light scattered from the view volume and produces signals proportional to the light sensed. Harmonic generators are used in alternate embodiments to produce sub-micron wavelengths. Optical coatings on mirrors forming cascaded cavities are used to isolate a harmonic wavelength in a cavity containing the view volume.

6 Claims, 3 Drawing Sheets

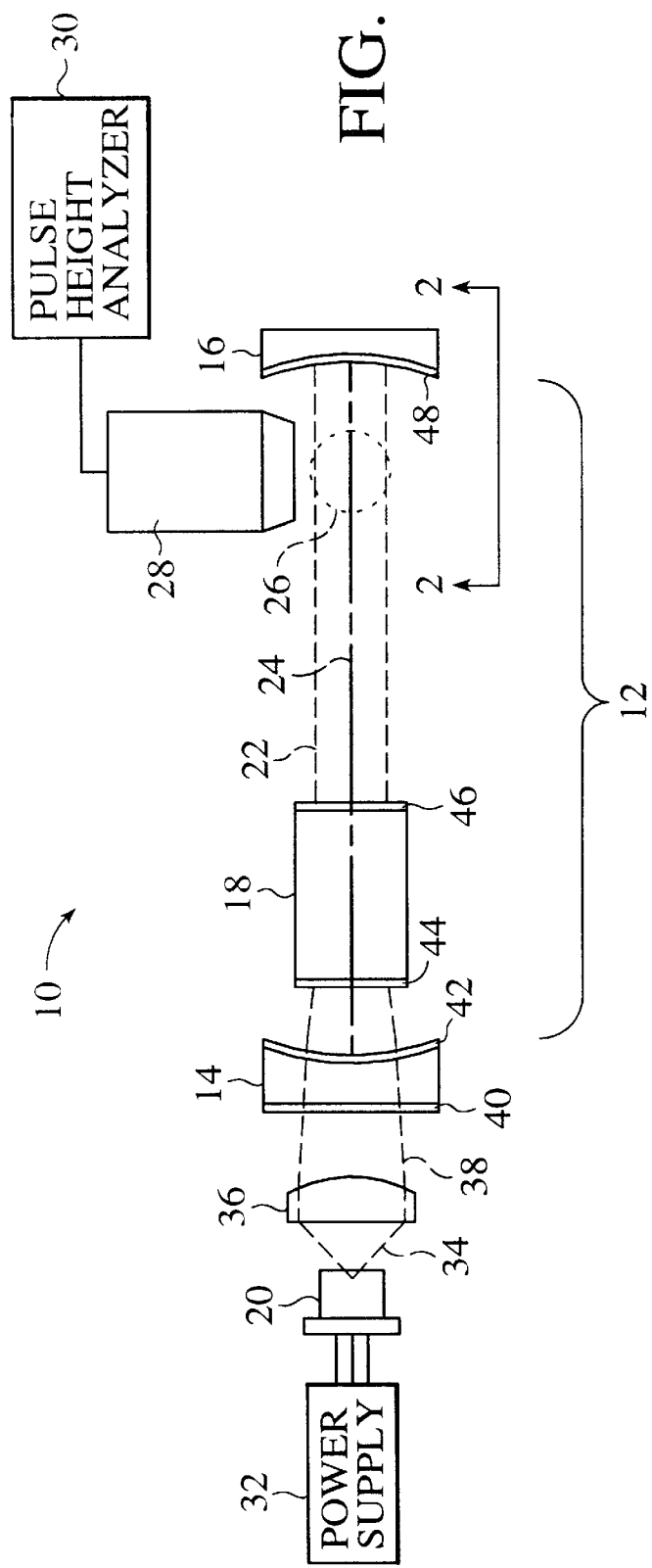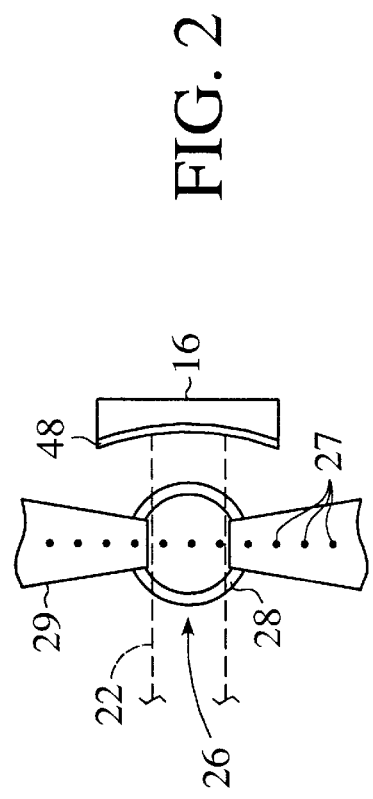

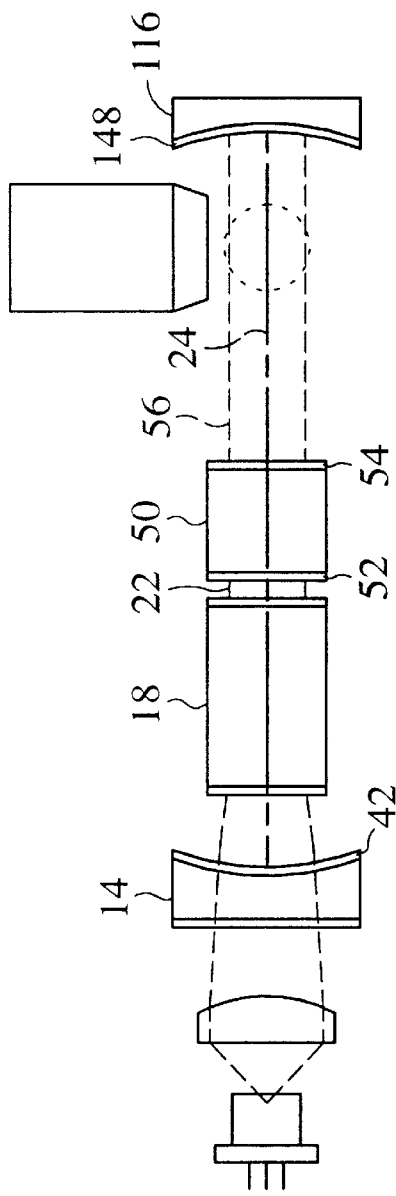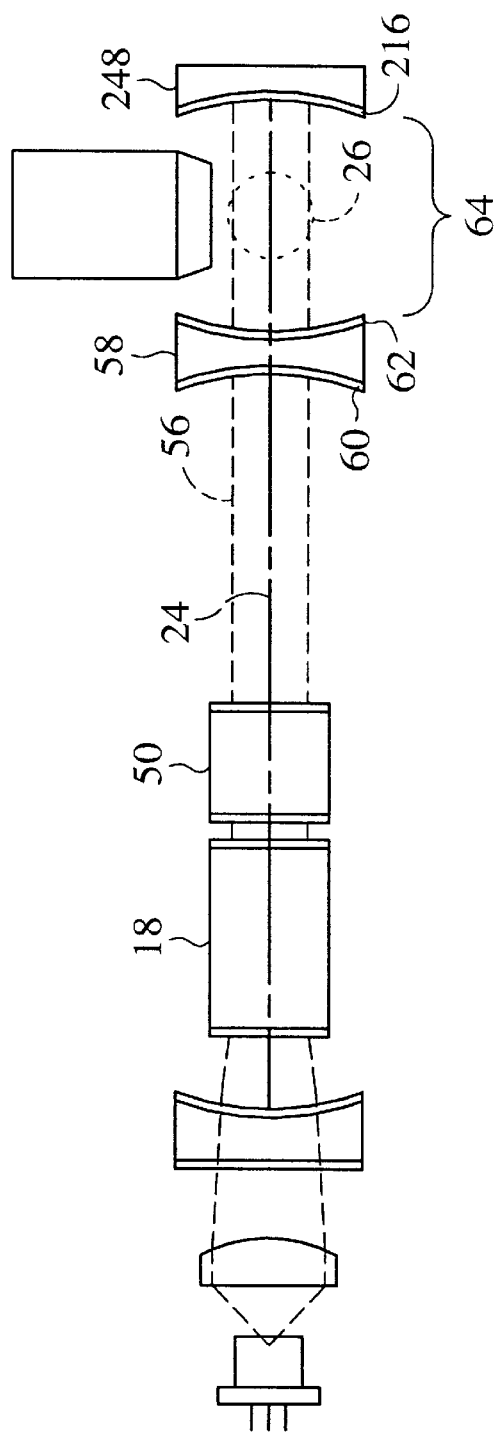

5,903,347

PARTICLE COUNTER EMPLOYING A CHROMIUM BASED SOLID-STATE LASER WITH AN INTRACAVITY VIEW VOLUME

CROSS-REFERENCE TO RELATED APPLICATION

This application is a continuation-in-part of U.S. patent application Ser. No. 08/614,814, filed Mar. 8, 1996, now U.S. Pat. No. 5,642,193, issued Jun. 24, 1997.

TECHNICAL FIELD

The present invention pertains to the field of particle counters. Specifically, the present invention pertains to an optical instrument for counting particles in a fluid stream.

BACKGROUND ART

Typically, particle detectors employ laser devices producing a beam of coherent light that is directed to impinge upon a sample of particles. Particle detection is achieved either by sensing light scattered by a particle, e.g. U.S. Pat. No. 5,085,500 to Blesener et al., or by detecting extinction of light, e.g. U.S. Pat. No. 5,121,988 to Blesener et al. U.S. Pat. No. 4,811,349 to Payne et al. discloses a chromium colquiriite such as $Cr:LiSrAlF_6$ as a useful laser crystal. U.S. Pat. No. 5,105,434 to Krupke et al. discloses a chromium colquiriite solid-state laser such as $Cr:LiSrAlF_6$ pumped with at least one AlGaAs semiconductor laser, and U.S. Pat. No. 5,249,189 to Scheps discloses a chromium colquiriite solid-state laser such as $Cr:LiSrAlF_6$ pumped with at least one visible AlGaAs semiconductor laser. U.S. Pat. No. 5,317,447 to Baird and DeFreez discloses, in pertinent part, a solid state laser having a $Cr:LiSrAlF_6$ crystal pumped from one end by an array of semiconductor laser diodes and suggests use of broad area laser diodes.

Particle detectors have been used for a variety of purposes to detect the presence and/or size of particles in various fluids, including air and other gases, as well as liquids, such as water, hydraulic oils and lubricants. They have proved particularly useful to control contamination in many industrial environments. For example, particulate contamination can cause hydraulic equipment and the like to fail due to excessive accumulation of particles in the hydraulic fluid. Even though filters are used in such equipment to continuously remove particles, the filters may become clogged and may rupture due to excess pressure build-up across the filter membrane. Also, microelectronic fabrication requires a "clean room" in which particulate contaminants, e.g., dust, are filtered from an atmosphere of a room. The filters used in "clean rooms" are also subject to clogging and compromise, resulting in particulate matter entering a "clean room" atmosphere in great quantities. Failure to provide a "clean room" results in particulate contamination of the devices during fabrication, which reduces yield. Particle detectors are thus used in such environments to detect particles in specified size classes and report the cleanliness level of the fluid according to categories specified by industry standards.

A significant amount of research has been performed using open cavity gas lasers in particle detection systems and is discussed by R. G. Knollenberg and B. Schuster in "Detection and Sizing of Small Particles in an open Cavity Gas Laser", *Applied Optics*, Vol. 11, No. 7, pp. 1515–1520 (November 1972). Sub-micron particle sizing devices utilizing light scattering in an open cavity laser device is described by R. G. Knollenberg and R. E. Leur in "Open Cavity Laser 'Active' Scattering Particle Spectrometry from 0.05 to 5 Microns", *Fine Particles, Aerosol, Generation Measurement, Sampling and Analysis*, Academic Press, pp. 669–696 (May 1975).

U.S. Pat. No. 4,594,715 to Knollenberg discloses an external cavity gas laser for use as a particle detector that includes first, second and third spaced mirrors. The first and second mirrors define an active resonant cavity of a gas laser, and the second and third mirrors define a second cavity. The second cavity ranges between being passive and being closely coupled as part of the active cavity, depending on the phase of the light returned from the third mirror to the second mirror. In the limiting case where the second cavity is not resonant, a large field does not build up in the passive cavity, because that cavity is off resonance for the wavelength of the active cavity. In the latter case, the second mirror, ignoring scattering and absorption losses in its coating and substrate, becomes transparent to light recirculating in the external cavity formed by the first and third mirrors, thus destabilizing the original cavity modes of the resonator formed by the first and second mirrors. In this case, even a small amount of absorption or scattering in the coating or substrate of the second mirror will result in the resonator formed by the first and third mirrors to have low net gain. This is because the inherent low gain of many types of gas lasers renders them particularly sensitive to intracavity loss. To address these issues, Knollenberg describes a method to modulate the external cavity along the laser axis, thereby creating a broad, Doppler induced, incoherent spectrum. This reduces the Q value of that cavity, because the nominal Q, as calculated from standard Fabry-Perot formulas, depends, for buildup of optical power, on having a resonance wavelength as opposed to a broad spectrum.

A problem with certain gas lasers is that they sometimes have a highly charged window, most of the time a Brewster window. A high voltage plasma inside of the tube creates a charge build-up on the outside of the window because the window is a very good insulator. This charge attracts oppositely charged molecules that get through purge filters. After a period of time (from 2 days to 2 weeks) depending on concentration, the build-up is a high enough loss that it causes loss in lasing power and inevitable catastrophic failure.

It is an object of the present invention to provide a resonant cavity type particle detector having improved efficiency with an optimized resonant cavity and which is not subject to the catastrophic failure mode of a gas laser.

SUMMARY OF THE INVENTION

These objects have been achieved by incorporating a chromium doped colquiriite solid-state crystal, such as a cylindrical, elongated $Cr:LiSrAlF_6$ crystal, into in a resonant cavity that includes an intra-cavity view volume. The resonant cavity is defined by two spaced apart mirrors, with the crystal positioned between them, defining a light path. A pump source is optically coupled to drive the crystal to produce coherent light having a first wavelength. The light is mostly confined to the cavity and very little escapes. So, the present apparatus is not a laser in the sense of having an output beam. Rather, a new use and a new apparatus have been discovered for the crystal material discovered by Payne et al.

The view volume is positioned intracavity in the beam path, between the first mirror and the lasing medium, to introduce particles, suspended in a flowing gaseous or liquid stream, into the resonant cavity so that light impinging thereupon produces scattered light. A detector is disposed to sense light scattered sideways from the view volume, i.e. transverse to the longitudinal axis of the cavity, and produces signals proportional to the light sensed. A displaying device, such as a pulse height analyzer, is in electrical communication to receive the signals produced by the detector to quantitatively display the intensity of the light sensed. In an alternate embodiment, a harmonic generator is disposed within the resonant cavity. The harmonic generator is disposed between the lasing medium and the view volume and shortens the wavelength of the light produced by the lasing medium that passes therethrough.

In another embodiment, the view volume is disposed in a second separate cavity unidirectionally optically coupled to the first resonant cavity. A harmonic generator may be disposed in the laser cavity to produce light having a second wavelength by shortening the wavelength of the light produced by the lasing medium. One of the mirrors forming a resonant cavity functions as a wavelength separator by reflecting light at the lasing wavelength while being transmissive with respect to light at the second wavelength. In this fashion, the second cavity may include light having only the second wavelength.

In still another embodiment, three cavities are formed. The first resonant cavity is optically coupled to a second cavity as described above. Disposed in the second or third cavity, however, is a second harmonic generator to produce light having a third wavelength by shortening light having the second wavelength. The second cavity is unidirectionally optically coupled to a third separate cavity, where the view volume is disposed. Wavelength separators partition the cavities where appropriate. For example, the second wavelength separator may be a mirror reflecting light having the second wavelength while being transmissive to light having the third wavelength. In this fashion, the third cavity may include light having only the third wavelength.

BRIEF DESCRIPTION OF THE DRAWINGS

FIG. 1 shows a simplified plan view of the present invention.

FIG. 2 shows a partial cross-sectional view of the view volume shown in FIG. 1 taken across lines 2—2.

FIG. 3 shows a simplified plan view of the present invention in accord with a first alternate embodiment.

FIG. 4 shows a simplified plan view of the present invention in accord with a second alternate embodiment.

BEST MODE FOR CARRYING OUT THE INVENTION

Figure 5:
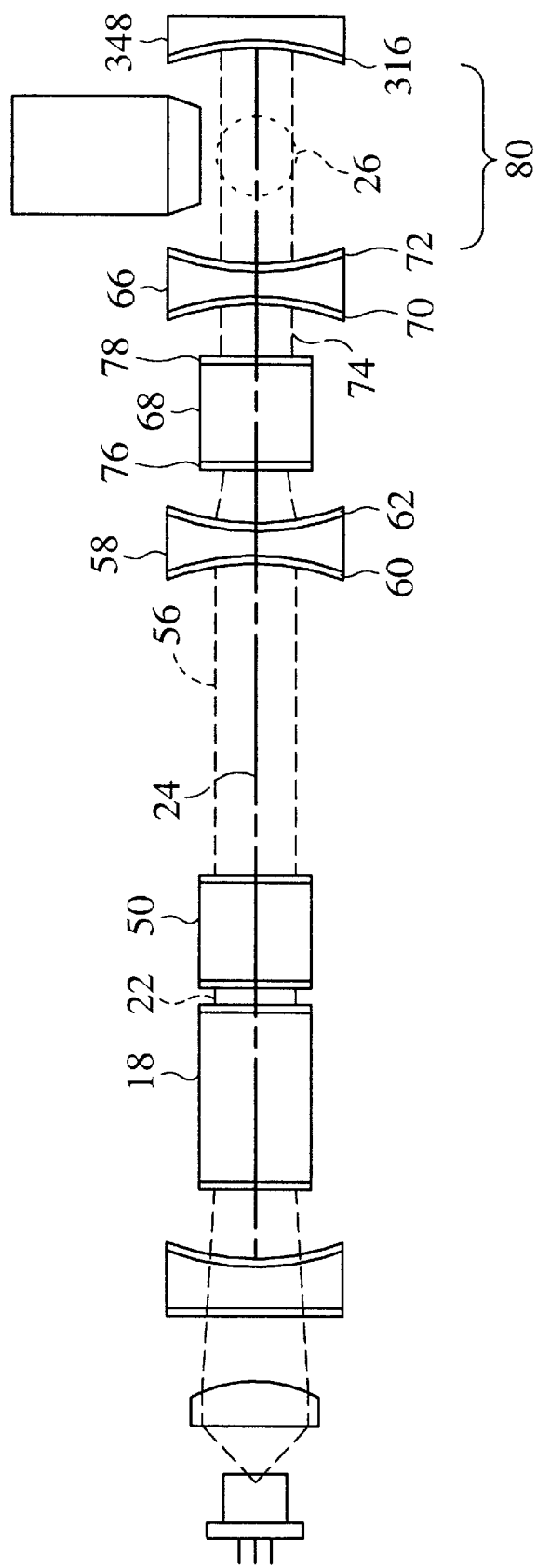
FIG. 5 shows a simplified plan view of the present invention in accord with a third alternate embodiment.

FIG. 1 shows a particle detector 10 in accord with the present invention, including a resonant cavity 12 defined by two spaced apart mirrors 14 and 16. A lasing medium 18 is positioned within the resonant cavity 12, between mirrors 14 and 16. The lasing medium is tunable chromium doped colquiriite, as described in U.S. Pat. No. 5,249,189 and incorporated by reference herein. A pump source 20 is optically coupled to drive the lasing medium 18 to produce coherent light 22 that propagates along a beam path 24, defined by the lasing medium 18. A view volume 26, defined by injector ports (not shown), is positioned in beam path 24 between mirror 16 and lasing medium 18. The injector ports introduce particles into view volume 26 so that light impinging upon particles in view volume 26 produces scattered light. A detector 28 is disposed to sense light scattered from view volume 26 and produces signals proportional to the light sensed. Typically, the detector is positioned to sense light scattered in a direction substantially perpendicular to both light path 24 and the longitudinal axis of view volume 26. A displaying device 30, such as a pulse height analyzer, is in electrical communication to receive the signals produced by detector 28 to quantitatively display the intensity of the light sensed. Note that most of the light does not go past mirrors 14 and 16.

Preferably, an optical pump source is employed that is capable of emitting light having a wavelength matching the absorption wavelength of the colquiriite crystal lasing medium 18. Beam shaping optics 36 are disposed in the path of coherent light 34, between mirror 14 and pump source 20, to produce a pump beam 38. Mirror 14 is transmissive with respect to the wavelength of pump beam 38, but preferably has an anti-reflective coating 40 disposed on a surface facing optics 36 to suppress reflection of the same. A dichroic coating 42 is disposed on a surface of mirror 14, opposing coating 40. Coating 42 exhibits the same properties as coating 40, with respect to beam 38. In this fashion, coatings 40 and 42 provide mirror 14 with highly transmissive surfaces through which a maximum intensity of pump beam 38 may pass.

In addition, an end of medium 18 facing mirror 14 includes a coating 44 which suppresses reflection of light having a wavelength approximating the emission wavelength, as well as light having a wavelength approximating the absorption wavelength of lasing medium 18. An end of medium 18, in opposing relation to coating 44, includes a coating 46 which also suppresses reflection of light having a wavelength approximating the emission wavelength. In this fashion, coatings 44 and 46 provide a highly transmissive surface through which a maximum intensity of beam 22 may pass.

The opposed ends of resonant cavity 12 is formed by coating 42 and coating 48, with coating 48 being disposed on mirror 16. Coatings 42 and 48 both provide optical properties to reflect most of the light having a wavelength approximating the wavelength of the light produced by lasing medium 18. In this manner, beam 22's egression from resonant cavity 12 is mostly blocked, thereby coupling cavity 12 with the pump source.

Referring also to FIG. 2, particles 27 are introduced into view volume 26 via a stream of fluent material, such as air, through the injector ports 29 so that light impinges on them. The particles scatter light, and a photo-detector 28, in optical communication with view volume 26, detects the scattered light. Detector 28 produces signals proportional to the light sensed. Pulse height analyzer 30 receives the signals and quantitatively displays the intensity of the light sensed. Negligible cavity losses result from the scattering of light by the particles due to their small size.

An advantage with preventing light 22 from exiting resonant cavity 12 is that this provides a greater amount of optical intensity to produce lasing action in lasing medium 18. This makes the particle detector less sensitive to optical loss caused from the scattering of light by particles present in view volume ark 26. This structure augments the inherent insensitivity of a solid-state laser to optical loss typically caused by intra-cavity optical surfaces, resulting in an improved power and stability.

The amount of light scattered from a particle having a diameter less than the wavelength of light impinging upon it is proportional to:

$D^6/\lambda^4$ where D is the particle diameter and λ is the wavelength of the scattered light. Therefore, to increase the amount of light scattered for a particle of a given size, it is desirable to decrease the wavelength λ of the light impinging thereupon. This is particularly useful to increase the resolution of the particle detector by making it more sensitive to particles of very small size. Decreasing the wavelength of light also facilitates characterizing the shape or dimensions of larger particles.

FIG. 3 shows an alternate embodiment of the present invention taking advantage of the aforementioned concepts. To shorten the wavelength of the light 22 emitted from lasing medium 18, a crystal harmonic generator 50 is disposed in light path 24, between mirror 116 and lasing medium 18. Dichroic coating 52 and coating 54 are present on opposite ends of the harmonic generator 50, providing highly transmissive surfaces through which light 22 may pass, as discussed above with respect to coatings 44 and 46. Typically, the crystal harmonic generator 50 is a frequency doubling crystal that shortens the wavelength of light 22 by 50%, producing light 56. Coating 52 also includes optical properties to reflect most of the light having a wavelength approximating 50% of the lasing wavelength. This effectively optically decouples light 56 from lasing medium 18 by preventing light 56 from passing through the same. In addition, coating 54 has optical properties to suppress reflectivity of light having a wavelength approximating 50% of the lasing wavelength. A coating 148 is disposed on mirror 116 having optical properties to reflect light having the wavelengths associated with beam 22 and light 56. In this fashion, light 56 is reflected between coatings 52 and 148. This increases the efficiency in the harmonic generator 50. Feedback of light 22 increases the intensity of light 56 proportional to the square of the intensity of light 22.

FIG. 4 is an alternate embodiment of the invention shown in FIG. 3 wherein a third mirror 58, having opposed major surfaces, is disposed between view volume 26 and harmonic generator 50. Third mirror 58 functions as a wavelength separator. To that end, the opposed surfaces of mirror 58 are coated with an antireflective coating 60 which suppresses reflectivity of light having a wavelength approximating 50% of the lasing wavelength. Dichroic coating 60 also reflects light having a wavelength approximating the lasing wavelength of the light produced by the lasing medium 18. Coating 62 is disposed on a surface of mirror 58, facing mirror 248, and is highly reflective at approximately 50% of the lasing wavelength. The surface of mirror 248, facing mirror 58, includes a coating 216 which is highly reflective to light approximating 50% of the lasing wavelength. In this fashion, a second cavity 64 is defined between mirrors 58 and 248, which is optically coupled to the remaining cavities in a unidirectional manner so that only light having a wavelength approximating 50% of the wavelength of the light produced by the lasing medium 18 is present therein. Thus, second cavity 64 allows detection of particles having a very small size, for the reasons discussed above with respect to FIGS. 1 and 2.

To further enhance the performance of the detector, an active length stabilization system may be employed. This would allow stabilization of the length of external cavities, such as cavity 64, to simultaneously promote high circulating power, while providing correct phase matching between cavities. In addition, mode matching optics, such as lenses, may be disposed to optically couple cavity 64 with the active cavity.

FIG. 5 shows a third alternate embodiment of the invention substantially similar to the embodiment shown in FIG. 4 with the addition of a fourth mirror 66 and a second harmonic generator 68, both of which are disposed in beam path 24. Fourth mirror 66 is disposed between view volume 26 and third mirror 58. Generator 68 is disposed between third 58 and fourth 66 mirrors to shorten the wavelength of the light emitted from harmonic generator 50. In this fashion, light 74, having a wavelength approximating 25% of the lasing wavelength, is produced. On a surface of generator 68, facing mirror 58, is a dichroic coating 76. Coating 76 is highly reflective to light 74 and suppresses reflection of light 56, effectively optically decoupling light 74 from generator 50 and medium 18 to provide the benefits discussed above with respect to FIG. 3.

On a surface of generator 68, opposing coating 76, is a coating 78 which suppresses reflection of light 56 and 74. A dichroic coating 70 is disposed on the surface of mirror 66, facing generator 68. Coating 70 is highly reflective to light 56 and suppresses the reflection of light 74. Having light 56 reflected back into generator 68 by coating 70 establishes a mode to maximize the optical energy from generator 68. On the surface of mirror 66, opposing coating 70, is a coating 72 that also suppresses reflection of light 74. In this fashion, coatings 70 and 72 provide mirror 66 with two highly transmissive surfaces through which light 74 may propagate. A coating 316 is disposed on a surface of mirror 348, facing coating 72. Coatings 316 and 72 are both highly reflective of light having a wavelength 25% of the lasing wavelength. Mirror 66 and 348 define a third cavity 80 coupled to the remaining cavities of the system so that most of the light having a wavelength 25% of the lasing wavelength is present therein.

The comparative wavelengths of a Cr:LiSrAlF$_6$ laser in the aforementioned particle detectors is as follows:

| Embodiment | Characteristic Wavelength (μm) In the View Volume |
|---|---|
| FIG. 1 | 0.830 |
| FIG. 4 | 0.415 |
| FIG. 5 | 0.208 |

Payne et al. disclose a broader class of crystal as an equivalent to colquiriite. This material is a chromium (Cr$^{3+}$) doped crystal of the formula XYZF$_6$, wherein X is selected from the group Li$^+$, Na$^+$, K$^+$, and Rb$^+$; Y is selected from the group Ca$^{2+}$, Sr$^{2+}$, Ba$^{2+}$, Cd$^{2+}$ and Mg$^{2+}$; Z is selected from the group Al$^{3+}$, Ga$^{3+}$ and Sc$^{3+}$. Such crystals are suitable for use in the present invention.

An advantage of the present solid state laser particle measurement device over a gas laser in a similar device is the solid state device has the capability of power stability by feedback from a power monitor. This is done by putting a photo diode in the output beam and using its signal to boost the power to the pump laser when the solid state laser decreases in power.

Anyone skilled in the art on laser design could conclude that high reflective and antireflective laser coatings could be put directly on the surfaces of the laser crystal or harmonic generators, eliminating the need for a separate optic.

We claim:

1. A particle counter, comprising:

a laser crystal of chromium colquiriite;

a pump source optically coupled to drive said laser crystal to produce a lasing wavelength of light;

first and second spaced apart mirrors defining a laser resonant cavity, with said laser crystal disposed in said cavity, said first and second mirrors each having a highly reflective surface, such that the mirrors confine substantially all of the light produced by said laser crystal therebetween;

view volume means within the laser resonant cavity in optical communication with said laser crystal, for introducing particles into said light path to produce scattered light; and a detector to sense light scattered from said view volume means and produce signals proportional thereto, the particle counter further having at least one harmonic generator means disposed in said light path for converting the lasing wavelength to a harmonic wavelength of the lasing wavelength and having a wavelength selective means associated with the harmonic generator for introducing said harmonic wavelength into said view volume having a predetermined wavelength.

2. The particle counter as recited in claim 1 wherein said first mirror is highly reflective of light produced by the laser crystal but transmissive of light from said pump source, the light from said pump source being optically coupled to the laser crystal through said first mirror, with beam shaping optics disposed between said dumd source and said first mirror.

3. The particle counter as recited in claim 1 wherein said view volume has a longitudinal axis extending transverse to said light path, and said detector is positioned to sense light scattered from the view volume.

4. A particle counter, comprising:

a laser chromium ($Cr^{3+}$) doped crystal of the formula $Cr^{3+}:XYZF_6$ wherein X is selected from the group $Li^+$, $Na^+$, $K^+$ and $Rb^+$, Y is selected from the group $Ca^{2+}$ $Sr^{2+}$, $Ba^{2+}$, $Cd^{2+}$ and $Mg^{2+}$, and Z is selected from the group $Al^{3+}$, $Ga^{3+}$ and $Sc^{3+}$;

a pump source optically coupled to drive said laser crystal to produce coherent light;

first and second spaced apart mirrors defining a laser resonant cavity, with said laser crystal disposed in said cavity, said first and second mirrors each having a highly reflective surface, such that the mirrors confine substantially all of the light produced by said laser crystal therebetween;

view volume means within the laser resonant cavity in optical communication with said laser crystal, for introducing particles into said light path to produce scattered light; and a detector to sense light scattered from said view volume means and produce signals proportional thereto, the particle counter further having at least one harmonic generator means disposed in said light path for converting the wavelength of the coherent light to a harmonic wavelength and having a wavelength selective means associated with the harmonic generator for introducing said harmonic wavelength into said view volume.

5. The particle counter as recited in claim 4 wherein said first mirror is highly reflective of light produced by the laser crystal but transmissive of light from said pump source, the light from said pump source being optically coupled to the laser crystal through said first mirror, with beam shaping optics disposed between said pump source and said first mirror.

6. The particle counter as recited in claim 4 wherein said view volume has a longitudinal axis extending transverse to said light path, and said detector is positioned to sense light scattered from the view volume.

* * * * *